(12) United States Patent
Daniel

(10) Patent No.: US 10,278,822 B2
(45) Date of Patent: *May 7, 2019

(54) PENILE PROSTHESIS KIT OF PARTS

(71) Applicant: Coloplast A/S, Humlebaek (DK)

(72) Inventor: Geoffrey A. Daniel, St. Paul, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/957,918

(22) Filed: Apr. 20, 2018

(65) Prior Publication Data

US 2018/0235761 A1    Aug. 23, 2018

Related U.S. Application Data

(63) Continuation of application No. 15/260,321, filed on Sep. 9, 2016, now Pat. No. 9,987,136.

(30) Foreign Application Priority Data

Aug. 21, 2017 (DK) .................... 2017 70630
Sep. 7, 2017 (EP) ..................... 17189841

(51) Int. Cl.
*A61F 5/00* (2006.01)
*A61F 2/26* (2006.01)

(52) U.S. Cl.
CPC ........ *A61F 2/26* (2013.01); *A61F 2250/0013* (2013.01)

(58) Field of Classification Search
CPC .................................... A61F 2/26; A61F 5/41
USPC ...................................... 600/38–41
See application file for complete search history.

(56) References Cited

U.S. PATENT DOCUMENTS

| | | | |
|---|---|---|---|
| 9,987,136 B2 * | 6/2018 | Daniel | A61F 2/26 |
| 2006/0135845 A1 * | 6/2006 | Kuyava | A61F 2/26 600/40 |
| 2011/0118540 A1 * | 5/2011 | Morningstar | A61F 2/26 600/40 |
| 2013/0072751 A1 * | 3/2013 | Fogarty | A61F 2/26 600/40 |

* cited by examiner

*Primary Examiner* — John P Lacyk
(74) *Attorney, Agent, or Firm* — Coloplast Corp., Coloplast A/S; Nick Baumann

(57) ABSTRACT

A penile prosthesis kit of parts includes an inflatable implant, a reservoir adapted to contain a volume of liquid, a pump, tubing and tubing connectors provided for attachment of the inflatable implant and the reservoir to the pump, and instructions for use provided for implantation and use of the pump. The pump has a rotary valve located in a first flow path entering into the pump and in a second flow path exiting from the pump. When implanted, the rotary valve is constrained to rotate in only one direction to move a portion of the volume of the liquid from the reservoir through the first flow path and through the second flow path into the inflatable implant.

10 Claims, 14 Drawing Sheets

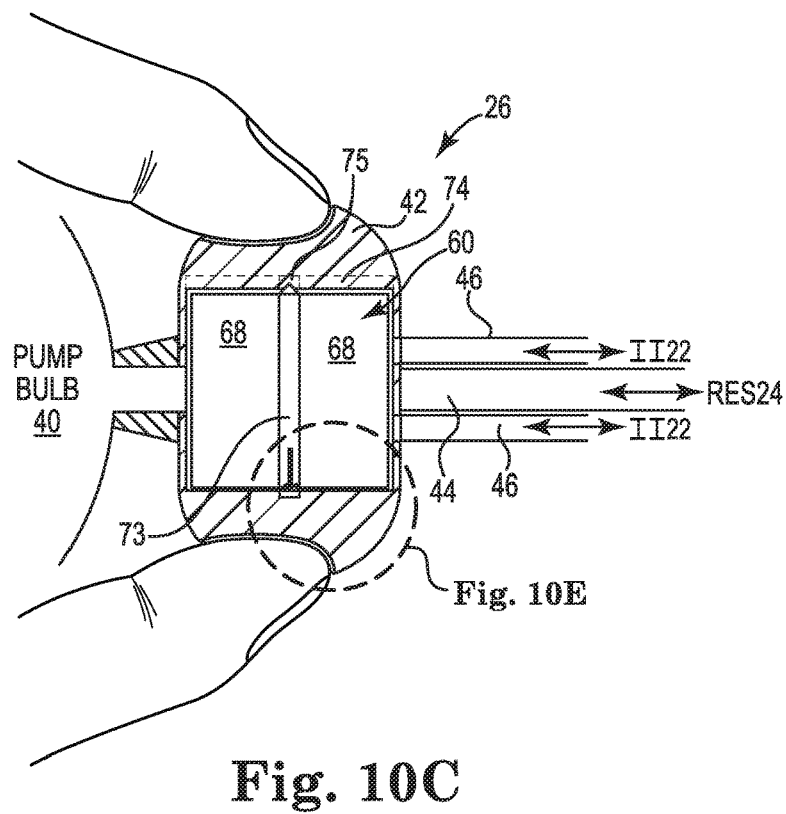
Fig. 10C
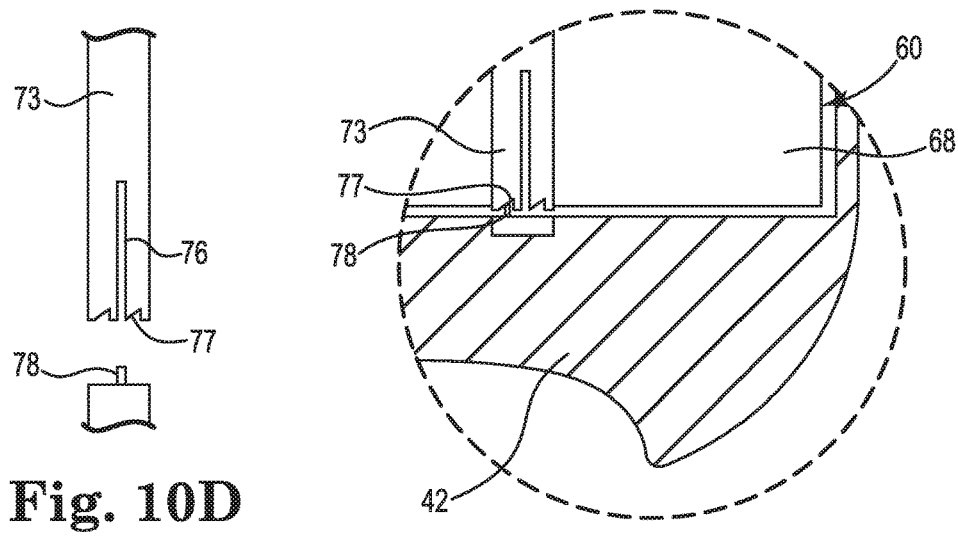
Fig. 10D
Fig. 10E

DEFLATION MODE

US 10,278,822 B2

PENILE PROSTHESIS KIT OF PARTS

BACKGROUND

An implanted penile prosthetic is a proven treatment in relieving erectile dysfunction in men.

A penile prosthetic typically includes two inflatable implants that are implanted in the corpora cavernosa of the penis, a reservoir implanted in the abdomen that communicates with the inflatable implant(s), and a pump, often located in the scrotum, that is employed to move liquid from the reservoir into the inflatable implant(s).

In a typical application, the user squeezes a bulb of the pump multiple times to sequentially transfer liquid from the reservoir to the inflatable implants. Each squeeze of the bulb ejects some liquid to the inflatable implants. The squeezed (compressed) bulb recovers, creating a suction pressure that draws additional liquid out of the reservoir and into the bulb. Subsequent squeezing and recovery of the bulb transfers the liquid collected in the bulb into the inflatable implants, which inflates the inflatable implants to provide the user with an erect penis. The user returns the penis to its flaccid state by selectively activating a deflation mechanism and transferring the liquid from the inflatable implant(s) back into the reservoir.

It is desirable to provide the user with a simple and efficient mechanism for addressing erectile dysfunction.

SUMMARY

A reservoir of an implanted penile prosthetic contains a liquid. A pump bulb is operable to move the liquid from the reservoir to inflatable implants. It is undesirable to have the liquid move from the reservoir directly into the inflatable implants without user input, such as by pumping the pump bulb. For example, a penile prosthetic user might inadvertently lean against an edge of a table and create a pressure increase inside the reservoir (implanted in the user's abdomen). The increase in pressure in the reservoir could potentially cause the liquid to flow directly from the reservoir to the inflatable implants, which might cause an unintended "auto-inflation" of the inflatable implants, and consequently, an unintended erection of the penis. Embodiments described below in this patent application provide solutions to the potential problem of auto-inflation of inflatable penile implants.

One aspect provides a pump for an implantable penile prosthetic, where the pump includes a valve that provides both an inflation feature and an anti-auto-inflation feature. The pump includes a reservoir tubing port, an inflatable implant tubing port, and a pump bulb connected to a body of the pump. The pump bulb is operable to move a liquid through the reservoir tubing port and into the pump bulb along a first flow path formed in the body of the pump, and out of the pump bulb and through the inflatable implant tubing port through a second flow path formed in the body of the pump. A rotary valve communicating with both of the first flow path and the second flow path is constrained to rotate in only one direction: either clockwise or counter clockwise. The rotation of the rotary valve operates to inflate the inflatable implants. The constrained movement of the rotary valve provides the pump with an anti-auto-inflation feature that prevents the liquid from moving from the reservoir to the inflatable implants without affirmative operation of the pump bulb. To this end, the pump prevents auto-inflation of the inflatable implants, and thus prevents unintended erection of the penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

FIG. 10C is a partial cross-sectional top view of one embodiment of the pump illustrated in FIG. 4 showing an embodiment of an axel providing lateral displacement of the valve in the body of the pump.

FIG. 10D is an enlarged view of a portion of the axel illustrated in FIG. 10C.

FIG. 10E is an enlarged view of a portion of the illustration of FIG. 10C.

DETAILED DESCRIPTION

Figure 1:
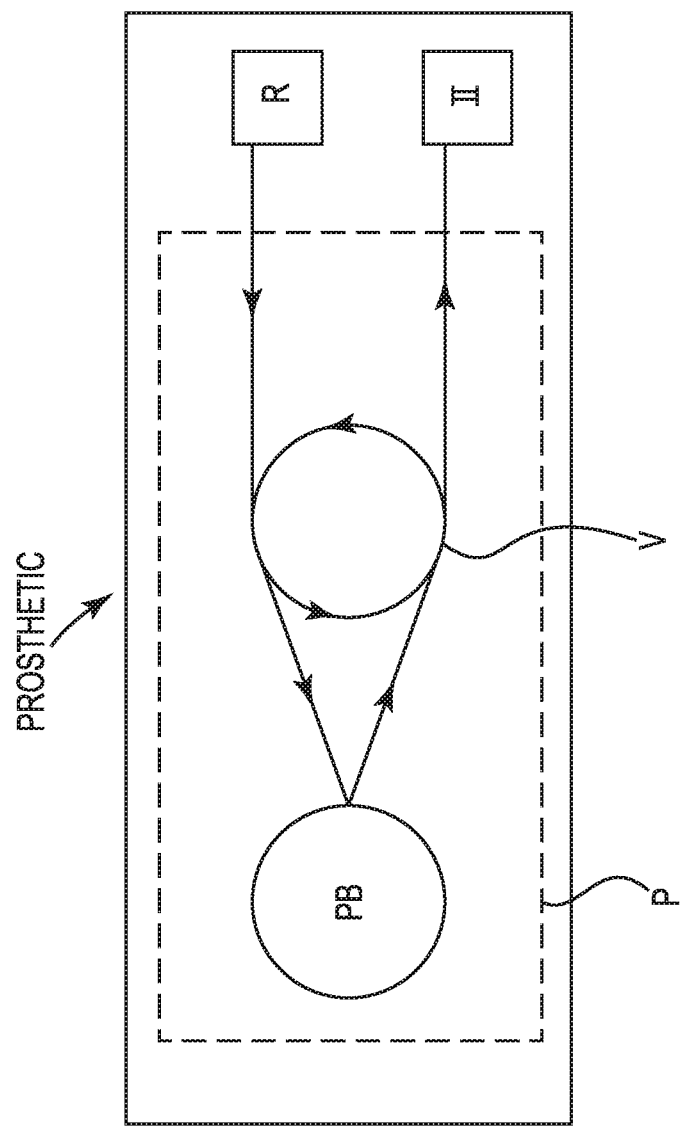
FIG. 1 is a schematic box diagram of one embodiment of a penile prosthetic having a pump providing an inflation feature and an anti-auto-inflation feature.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other, unless specifically noted otherwise.

The term "rotary valve" means a valve that is rotatable through 360 degrees such that portions of the valve spin on an axis entirely around a circular pathway.

"Auto-inflation" means an unintended inflation of an inflatable implant of a penile prosthetic. Autoinflation occurs, for example, when a pressure external from the prosthetic is directed to a reservoir of the prosthetic, and the pressure of the liquid inside of the reservoir causes the liquid to flow out of the reservoir directly to the inflatable implants, and thus bypassing the user-activated pump bulb. The consequence is an unintended and undesirable erection of the penis.

"Anti-auto-inflation" means a device that prevents the unintended inflation of an inflatable implant of a penile prosthetic (auto-inflation).

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12-inch ruler has a center at 6 inches, a first end at zero inches and a second, opposite end at 12 inches, an end portion adjacent to the first end and another end portion adjacent to the second end.

Embodiments provide a pump that has a rotary valve that rotates in only one direction to deliver liquid along a flow path in that one direction, which is useful when inflating an inflatable implant with the liquid. The rotary valve rotates in one and only one direction, which prevent the liquid from flowing back through the pump, and this attribute provides an anti-auto-inflation feature to the pump.

Embodiments provide a pump having an anti-auto-inflation feature provided by a rotary valve enclosed inside of a housing, where the housing is deformable by finger pressure to form a gap between the rotary valve and the housing. The rotary valve incorporates the anti-auto-inflation feature and the deformable housing in combination with the rotary valve provides the pump with a deflation mechanism.

Embodiments provide a pump with two possible deflation mechanisms, the deformable housing/rotary valve referenced above, and an additional deflation mechanism provided by a spring-biased valve stem and crown.

Embodiments provide a pump having an anti-auto-inflation feature provided by a rotary valve that is prevented from rotating in one direction by a stop ledge.

Embodiments provide a pump having an anti-auto-inflation feature provided by a rotary valve that is prevented from rotating in one direction by a stop ledge, where the anti-auto-inflation feature is engineered to have a redundant feature where liquid exiting the reservoir is directed to impinge on a vane of the rotary valve to ensure the valve is "locked" into the anti-auto-inflation mode.

Embodiments provide a pump having a pump bulb that is flexible and includes a ribbed accordion structure. One advantage of a flexible bulb is that those with limited dexterity are able to easily squeeze the bulb when inflating the implanted prosthetic. One advantage of the ribbed structure is that the bulb is easy to control and grasp through the skin of the scrotum.

Embodiments provide a prosthetic having a reservoir formed to provide a "cloverleaf" style. One advantage of a cloverleaf style of reservoir is that the surgeon may collapse and fold the reservoir into a small unit that is implantable ectopically in small spaces, even outside of the pelvis.

Embodiments provide a pump having deflation surfaces that include a high-friction structure. One advantage of providing the deflation pads with such a structure is that the user is able to locate and use the deflation pads through the skin of the scrotum.

FIG. 1 is a schematic box diagram of one embodiment of a penile prosthetic having a pump P providing an inflation feature and anti-auto-inflation feature. The pump P of the prosthetic is connected to a reservoir R and an inflatable implant II. A pump bulb PB is connected to a body of the pump P and is operable to move liquid from the reservoir R into the inflatable implant II. The pump has a rotary valve V in the flow path between the reservoir R and the inflatable implant II. The rotary valve V is constrained to rotate in only one direction, which in this example is the counter clockwise direction. Rotation of the rotary valve V provides an inflation feature characterized by the movement of the liquid from the reservoir, into the pump bulb PB, and subsequently into the inflatable implant II. The one-directional movement of the rotary valve V provides the pump P with an anti-auto-inflation feature that prevents the liquid from moving from the reservoir directly into the inflatable implants, for example if the reservoir R is suddenly squeezed or pressurized. This attribute of the pump prevents auto-inflation of the inflatable implants, and thus prevents unintended erection of the penis. Deflation assemblies are described to deflate the implants and return the liquid from the implants to the reservoir.

Figure 2:
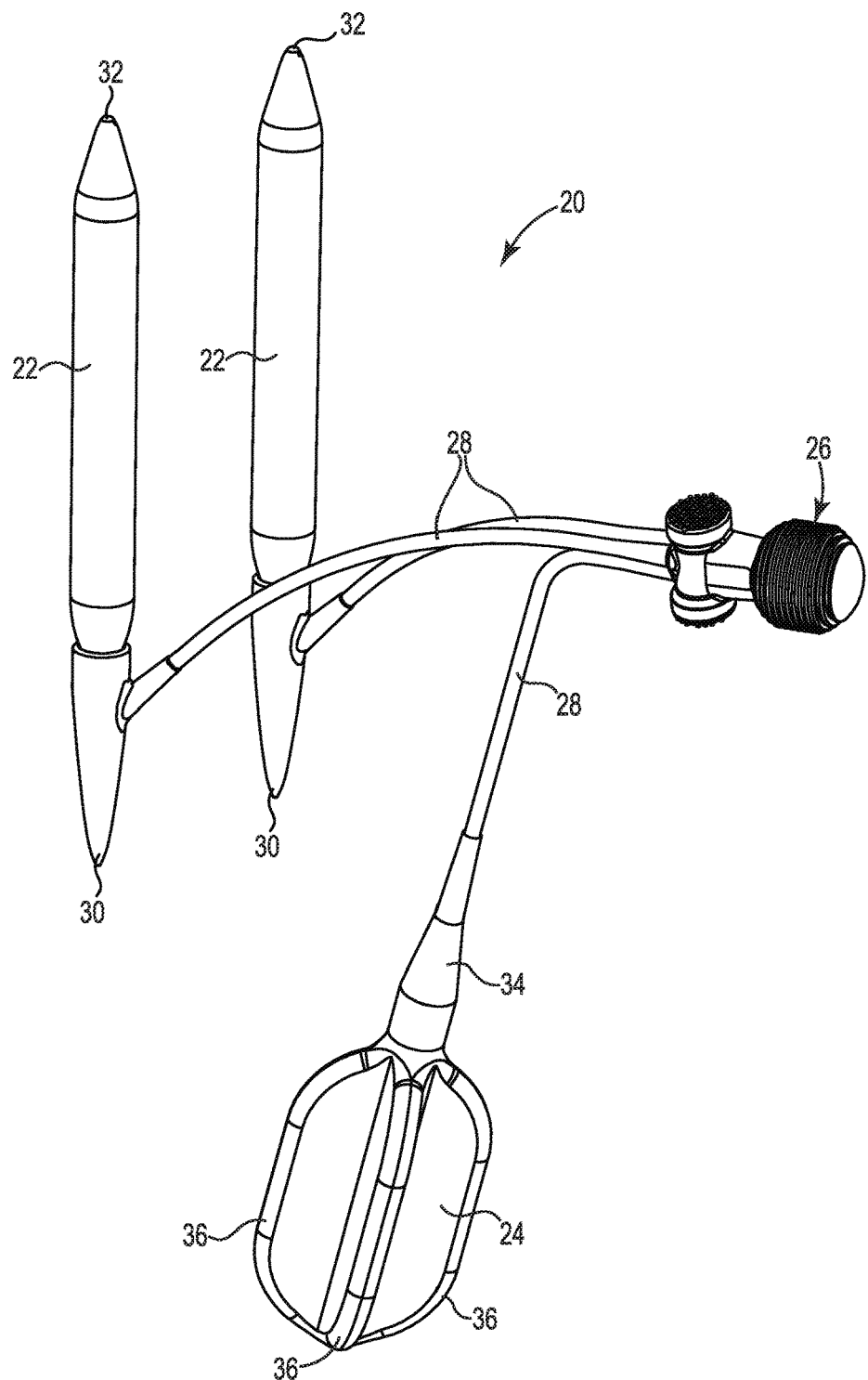
FIG. 2 is a perspective view of one embodiment of a penile prosthetic having a pump that has been connected to two inflatable implants and a reservoir.

FIG. 2 is a perspective view of one embodiment of a penile prosthetic 20 after assembly, for example as assembled by a surgeon in the course of implantation. The penile prosthetic 20 includes inflatable implants 22, a reservoir 24, and a pump 26 connected to the inflatable implants 22 and the reservoir 24, for example by kink resistant tubing 28.

Each of the inflatable implants 22 is sized for implantation into a corpora cavernosum within the penis. Each of the inflatable implants 22 includes a proximal end 30 opposite a distal end 32. During implantation, the proximal end 30 (also called a rear tip) is implanted into the crus of the penis and the distal end 32 is implanted within the glans penis. The inflatable implants 22 are configured to lose rigidity when deflated to provide the penis with a flaccid state, and expand and become rigid when the inflatable implants 22 are inflated with liquid to provide the penis with an erection. As a point of reference, the inflatable implants 22 are illustrated in an inflated state. Suitable material for fabricating the inflatable implants 22 includes silicone, biocompatible polymers such as urethanes, and blends of polymers with urethane, copolymers of urethane, or the like. Suitable inflatable implants are available from Coloplast Corp., Minneapolis, Minn.

The reservoir 24 is sized to maintain a volume of liquid between about 50-300 ml and includes a neck 34 that is smoothly coupled with the kink resistant tubing 28. In one embodiment, the reservoir 24 is provided as a "cloverleaf" style of reservoir having multiple leafs 36 that may be folded one against the other to compact the reservoir 24 for implantation into the abdomen of the user. One suitable reservoir 24 is sized to retain approximately 130 mL of liquid and is available from Coloplast Corp., Minneapolis, Minn.

Figure 3:
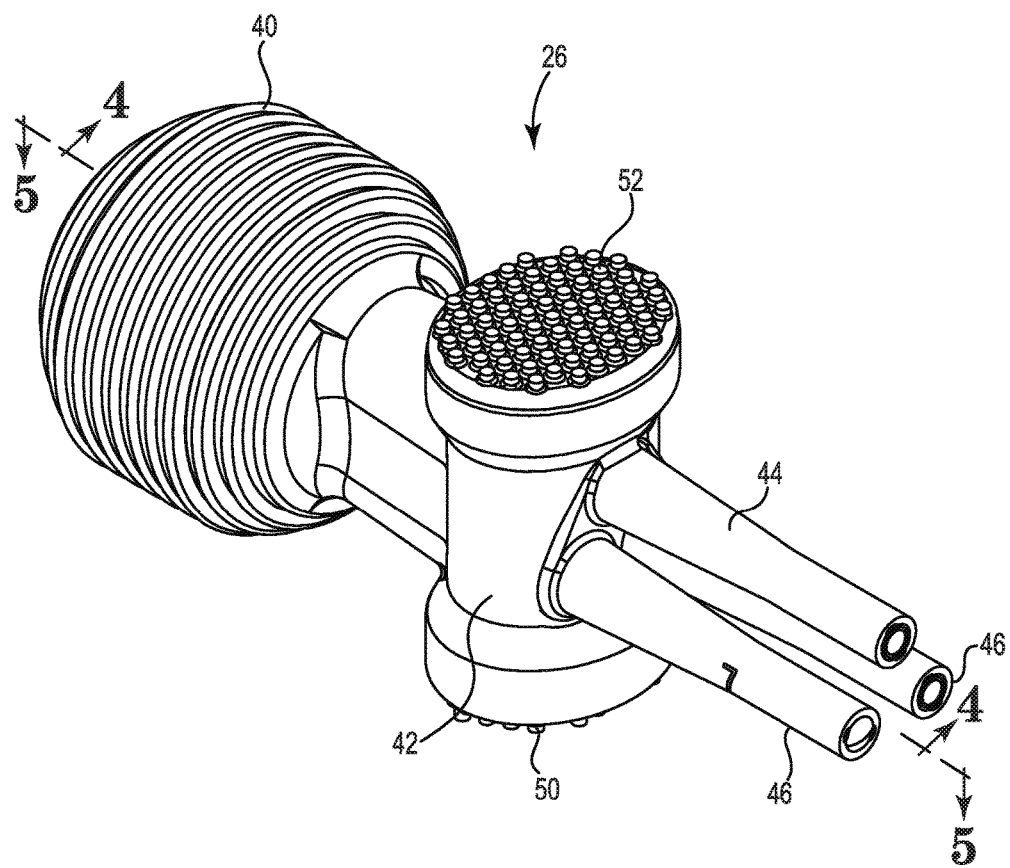
FIG. 3 is a perspective view of one embodiment of the pump illustrated in FIG. 2.

FIG. 3 is a perspective view of the pump 26. The pump 26 includes a pump bulb 40 connected to a pump body 42, a reservoir tubing port 44 connected with the pump body 42, and a pair of inflatable implant tubing ports 46 extending from the pump body 42.

In one embodiment, the pump bulb 40 is flexible and includes a ribbed accordion structure that allows the pump bulb 40 to collapse when squeezed to drive liquid out of the pump bulb 40, through the pump body 42, and out of the inflatable implant tubing ports 46. The accordion structure allows the pump bulb 40 to be operable by those who might have limited dexterity and to recover after being squeezed, which results in an expansion of the bulb 40. Expansion of the pump bulb 40 creates a negative local pressure in the bulb 40 that draws liquid out of the reservoir 24 (FIG. 2), through the reservoir tubing port 44 and the pump body 42, and into the pump bulb 40. Subsequent squeezing of the pump bulb 40 ejects liquid from the pump bulb 40 to the inflatable implants 22, and draws liquid back into the pump bulb 40 in a cyclical manner.

In one embodiment, the pump body 42 is integrally formed and connected with the pump bulb 40 and includes a first deflation surface 50 opposite a second deflation surface 52. The deflation surfaces 50, 52 (also called deflation pads) are illustrated as non-circular (elliptical) although other shapes for the deflation surfaces 50, 52 are also acceptable. The pump body 42 houses or maintains one or more valves (described below) that may be activated/deactivated by pressing the deflation surfaces 50, 52.

The reservoir tubing port 44 is configured to be connected to the reservoir 24 (FIG. 2) during implantation by the tubing 28. Each of the inflatable implant tubing ports 46 is connected to a respective one of the inflatable implants 22 via the tubing 28. A closed system is formed when the prosthetic is assembled, with the reservoir 24 containing the liquid that is moved into and out of the implants 22. Compressing the pump bulb 40 ejects the liquid from the bulb 40 through the inflatable implant tubing ports 46 to the inflatable implants 22, and expansion of the pump bulb 40 creates suction that draws liquid from the reservoir 24 through the pump body 42 and the reservoir tubing port 44 at a low velocity for delivery into the pump bulb 40.

Generally, the pump 26 is implanted into the scrotum of the user and connected to the inflatable implants 22 that are implanted into the penis of the user. The reservoir 24 is connected to the inflatable implants 22 and to the pump 26, and implanted within the abdomen of the user after verification that the connections are leak-free. The pump 26 is fabricated from material suitable for body implantation, such as silicone or the urethane-based materials described above for the inflatable implants 22 or the reservoir 24.

Figure 4:
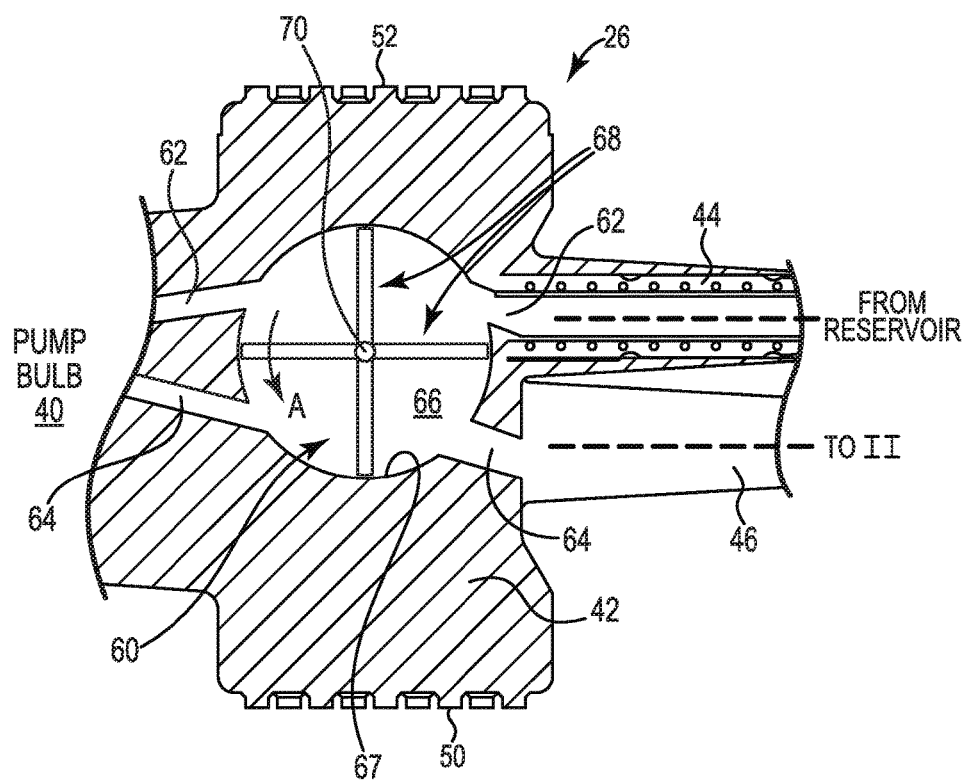
FIG. 4 is a partial cross-sectional view of the pump illustrated in FIG. 3 showing a rotary valve providing an inflation feature and an anti-auto-inflation feature.
Figure 5:
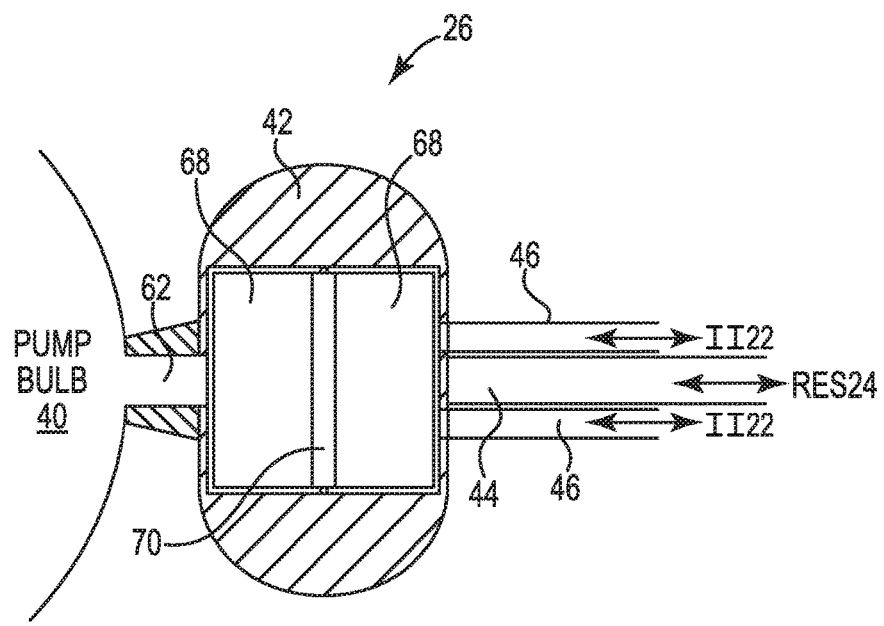
FIG. 5 is a top schematic view of the pump and the rotary valve illustrated in FIG. 4.

FIG. 4 is a partial cross-sectional side view and FIG. 5 is a partial cross-sectional top view of the pump 26. The pump 26 includes a rotary valve 60 providing the pump with both inflation and anti-auto-inflation attributes. The pump 26 is provided with a first flow path 62 formed in the body 42 between the reservoir tubing port 44 and the pump bulb 40, and a second flow path 64 formed in the body 42 between the pump bulb 40 and the inflatable implant tubing port 46. The rotary valve 60 is located in a cylindrical recess 66 that is formed in the pump body 42 to communicate with both of the first flow path 62 and the second flow path 64. The recess 66 forms a wall 67 that provides a valve seat against which the valve 60 seals.

The rotary valve 60 is constrained by the structure of the pump body 42 to rotate in only one direction, clockwise or counter clockwise. In the embodiment of FIG. 4, the rotating valve 60 is configured to rotate in only in the counter clockwise direction (arrow A) so that the liquid in the first flow path 62 is directed into the pump bulb 40, and subsequently exhausted from the pump bulb 40 into the second flow path 62 toward the inflatable implants II. The rotary valve 60 is prevented from rotating in a clockwise direction, and this constraint prevents the flow of liquid directly from the reservoir 24 into the inflatable implants 22, which provides the pump 26 with an anti-auto-inflation feature. The rotary valve is an anti-auto-inflation valve that is configured to prevent the liquid from moving through the inflatable implant tubing port without operation of the pump bulb, which advantageously provides a solution to the undesirable auto-inflation that can occur if the reservoir becomes suddenly over-pressurized.

The rotary valve 60 is inserted into and sealed within the cylindrical recess 66. It is acceptable to insert the rotary valve 60 through a side of the pump body 42, and subsequently seal the side of the pump body over the rotary valve 60. In one embodiment, the rotary valve 60 is over-molded and integrated within the pump body 42 during a molding process. In any regard, the wall 67 of the recess 66 provides a valve seat against which the rotary valve 60 is seated.

In one embodiment, cylindrical recess 66 is formed in the pump body 42 to intersect both of the first flow path 62 and the second flow path 64. The central location of the valve 60 between the bulb 40 and the ports 44, 46 allows the valve 60 to pull liquid out of the reservoir tubing port 44 and exhaust the liquid into the inflatable implant tubing ports 44. In one embodiment, cylindrical recess 66 is formed in the pump body 42 to be orthogonal to both of the first flow path 62 and the second flow path 64.

The reservoir tubing port 44 and the inflatable implant tubing ports 46 are formed on a first side of the body 42 of the pump 26 and the pump bulb 40 is connected to a second side of the body 42 opposite from the first side, and this advantageously separates the flow paths 62, 64 and also aligns the second flow path 64 with the bulb 40 and the inflatable implant tubing ports 46.

The rotary valve 60 includes a plurality of vanes 68 that extend radially away from a central axis 70 (or axel 70). In one embodiment, the rotary valve 60 includes four vanes as illustrated. The rotary valve 60 is suitably fabricated to include two or more vanes, for example 6 or 8 vanes, depending upon the design choice implemented when fabricating the pump 26. In one embodiment where the rotary valve 60 includes two vanes, the valve 60 is configured to rotate from a first configuration where the two vanes are horizontal to a second configuration where the two vanes are also horizontal (but with a 180-degree rotation), which could be described as a two-stroke set up. In this manner, the first flow path 62 is separated from the second flow path 64 by the two horizontal vanes, which prevents the direct flow of liquid from the reservoir R to the inflatable implants II.

The rotary valve 60 provides the pump 26 with a rotary exhaust valve, where the exhaust is in reference to the liquid that is moved from the pump bulb 40 to the inflatable implants II. The rotary valve 60 operates as described above to control and lock the pressure in the reservoir 24 (a lock-out feature). The lock-out feature is integrated as the valve inside of into the pump 26, as opposed to the reservoir 24 or other location, which advantageously reduces the number of parts in the prosthetic (no springs or push buttons, etc.). The rotary valve 60 is allowed to rotate in one direction and prevented from rotating in the opposite direction, and this attribute serves as an anti-auto-inflation feature for the pump 26 as well as a pressure hold lock for the implants 22.

Figure 6:
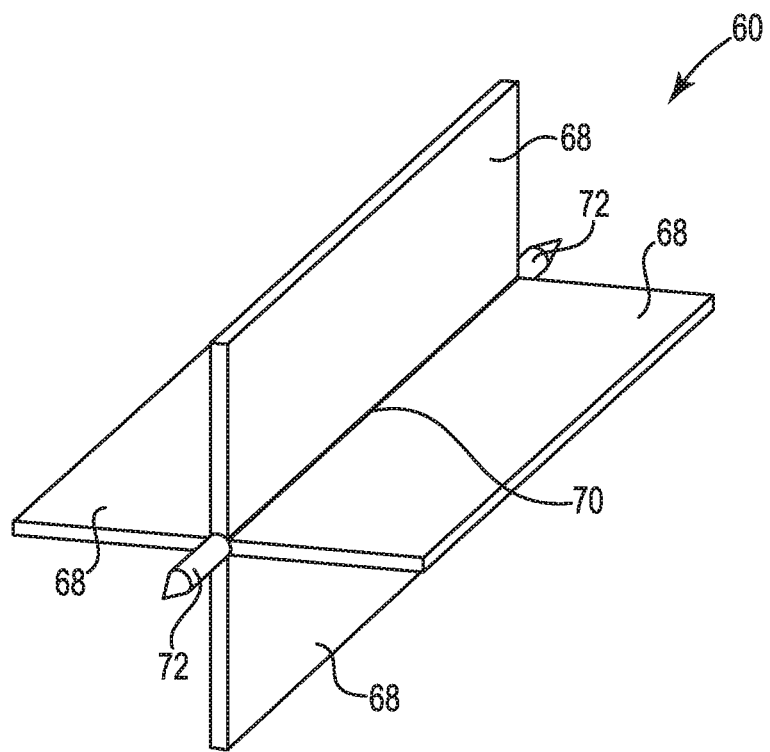
FIG. 6 is a perspective view of one embodiment of a rotary valve operable in the pump illustrated in FIGS. 3-4.

FIG. 6 is a perspective view of the rotary valve 60. This embodiment of the rotary valve 60 includes four orthogonal and planar vanes 68 each extending a uniform distance away from the central axel 70. In one embodiment, the axel 70 is provided with a pair of opposing trunnions 72. The trunnions 72 allow the rotating valve 60 to rotate within the recess 66. In one embodiment, the trunnions 72 are fabricated from a hard metal such as stainless steel to provide a low friction interface with the polymeric material of the pump body 42, which allows low friction rotation of the valve 60 inside of the pump 26. In one embodiment, the axel 70 or the trunnions 72 include bearings that allow the axel 70 to rotate relative to the pump body 42 with little or no friction.

Figure 7:
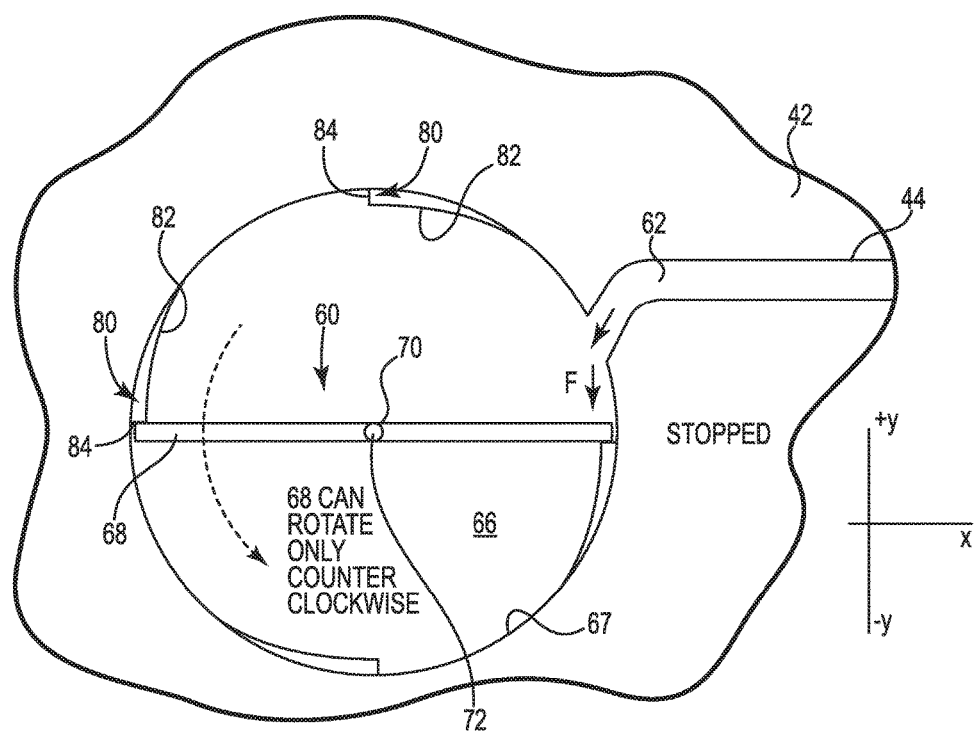
FIG. 7 is a cross-sectional side view of one embodiment of a stop ledge formed in a body of a pump located relative to one vane of a rotary valve.

FIG. 7 is a cross-sectional view of one embodiment of the cylindrical recess 66 formed in the pump body 42. The rotary valve 60 is constrained to rotate in one direction only, in this example the counter clockwise direction. Although the rotary valve has been illustrated as including four vanes 68, just two vanes 68 of the rotary valve 60 are illustrated in FIG. 7 for simplicity and clarity of the illustration. The recess 66 is fabricated to include a stop ledge 80 that allows the vanes 68 of the rotary valve 60 to rotate uni-directionally in a counter clockwise direction, but prevents the vanes 68 of the rotary valve 60 from rotating in a clockwise direction. The stop ledge 80 includes a converging face 82 that terminates in a stop face 84. Each vane 68 is configured to move along the converging face 82 and to drop off the stop ledge 80, thus engaging with the stop face 84. In this position, the vane 68 is prevented from rotating in the opposite direction (clockwise).

In one embodiment, the first flow path 62 that is formed in the body 42 and through the reservoir tubing port 44 is angled to have a force component that is directed into the vane 68 in a manner that pushes the vane 68 into the stop ledge 80. Unintended over-pressurization of the reservoir 24 can potentially send an amount of liquid jetting into the valve 60. Embodiments provide for the directional formation of the first flow path 62 so that any over-pressurized liquid escaping from the reservoir is directed into the valve 60 in a direction that acts to lock the vanes 68 against the stop ledge 80. This is to say that the force vector F of the flow of the liquid out of the reservoir 24 that results from a sudden over-pressurization of the reservoir 24 is configured to have a predominant-Y component according to the orientation of FIG. 7. Unintended over-pressurization of the reservoir 24 acts to lock the valve 60, while the usual squeezing of the pump bulb 40 rotates the valve 60 uni-directionally. For example, the sequential squeezing of the pump bulb 40 draws liquid out of the reservoir to substantially fill the space between the vanes 68 such that the pressure between the vanes is balanced. The relatively lower pressure in the expanding bulb 40 compared to the pressure behind the valve 60 acts to draw the liquid into the bulb 40 and out of the reservoir 24. The unintended over-pressurization of the reservoir 24, for example by the user leaning his abdomen against a table edge, sends liquid against the rotational direction of the valve 60 and advantageously locks the valve 60 (referred to as a lock-out feature).

Providing the rotary valve with a plurality of vanes advantageously provides a solution to auto-inflation by ensuring that a vane will be located where it can react to the force vector F associated with over-pressurization of the reservoir.

Positioning the rotary valve in a recess formed in the body of the pump and providing a stop ledge to prevent rotation of the rotary valve in one direction advantageously provides a solution to undesirable auto-inflation, and also simplifies the mechanism of the pump assembly.

Figure 8:
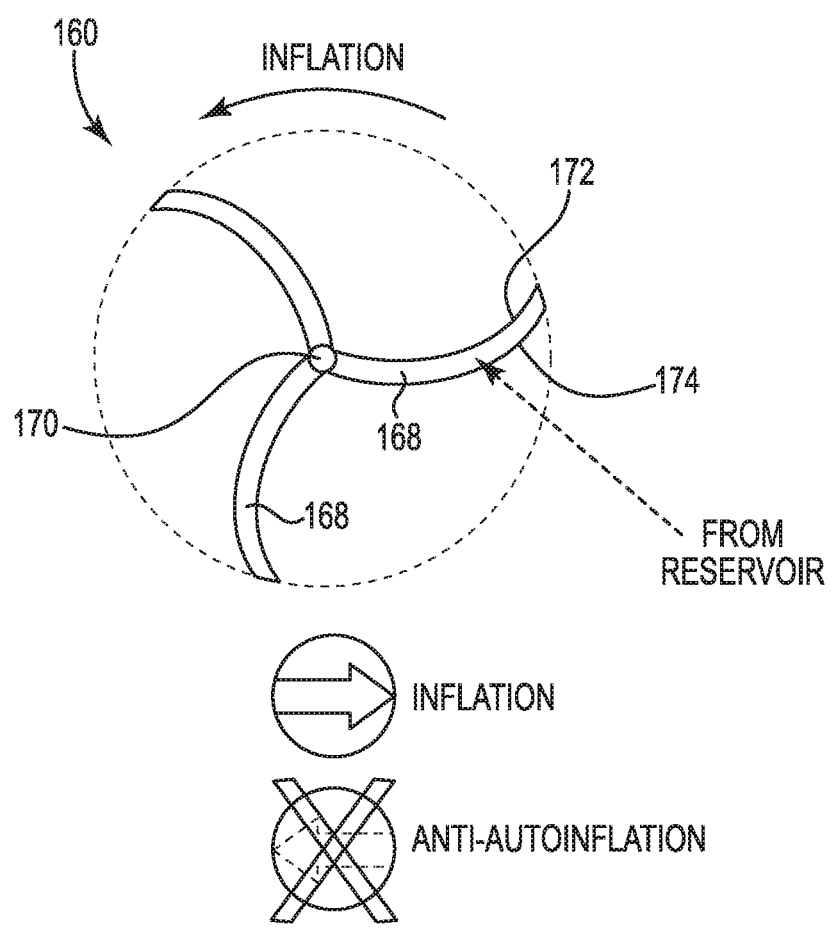
FIG. 8 is a side schematic view of one embodiment of a rotary valve operable in the pump illustrated in FIG. 3.

FIG. 8 is a side schematic view of one embodiment of a rotary valve 160 operable in the pump 26. The rotary valve 160 includes three vanes 168, where each of the veins 168 extends in a radial direction away from a central axel 170. The vanes 168 include a curvature that is configured to more efficiently sweep the liquid in the inflation direction. In one embodiment, each of the vanes 168 includes a leading face 172 opposite from a trailing face 174. The leading face 172 engages with the liquid from the reservoir and sweeps it in the direction of the inflatable implants. The trailing face 174 of each vane 168 is exposed to the flow path formed between the reservoir and the pump bulb. The liquid in the flow path between the reservoir in the pump bulb impinges upon the trailing face 174 to push the rotary valve 160 in a counter clockwise direction. In other words, the forces of the liquid leaving the reservoir push and contribute to the momentum of the rotary valve 160 rotating in the counter clockwise direction. The pump is provided with a stop feature, similar to the stop ledge 80 described above, that prevents the rotary valve 160 from rotating in a clockwise direction. For example, force vectors that are normal (or have a component that is normal) to the leading face 172 of each vane 168 result in the rotary valve 160 being stopped by the stop feature. The result is that force vectors incident to the trailing face 174 contribute to the momentum of the rotary valve 160, and force vectors that have a component that is normal to the leading face 172 result in the rotary valve 160 being locked relative to the stop feature, which is referred to as a lockout feature. The lockout feature is represented by the icons for "inflation" and "anti-autoinflation." Rotation in the counter clockwise direction results in the rotary valve 160 operating in the inflation mode, and forces acting in the clockwise direction relative to the vanes 168 result in the rotary valve 160 experiencing the anti-autoinflation mode.

Figure 9:
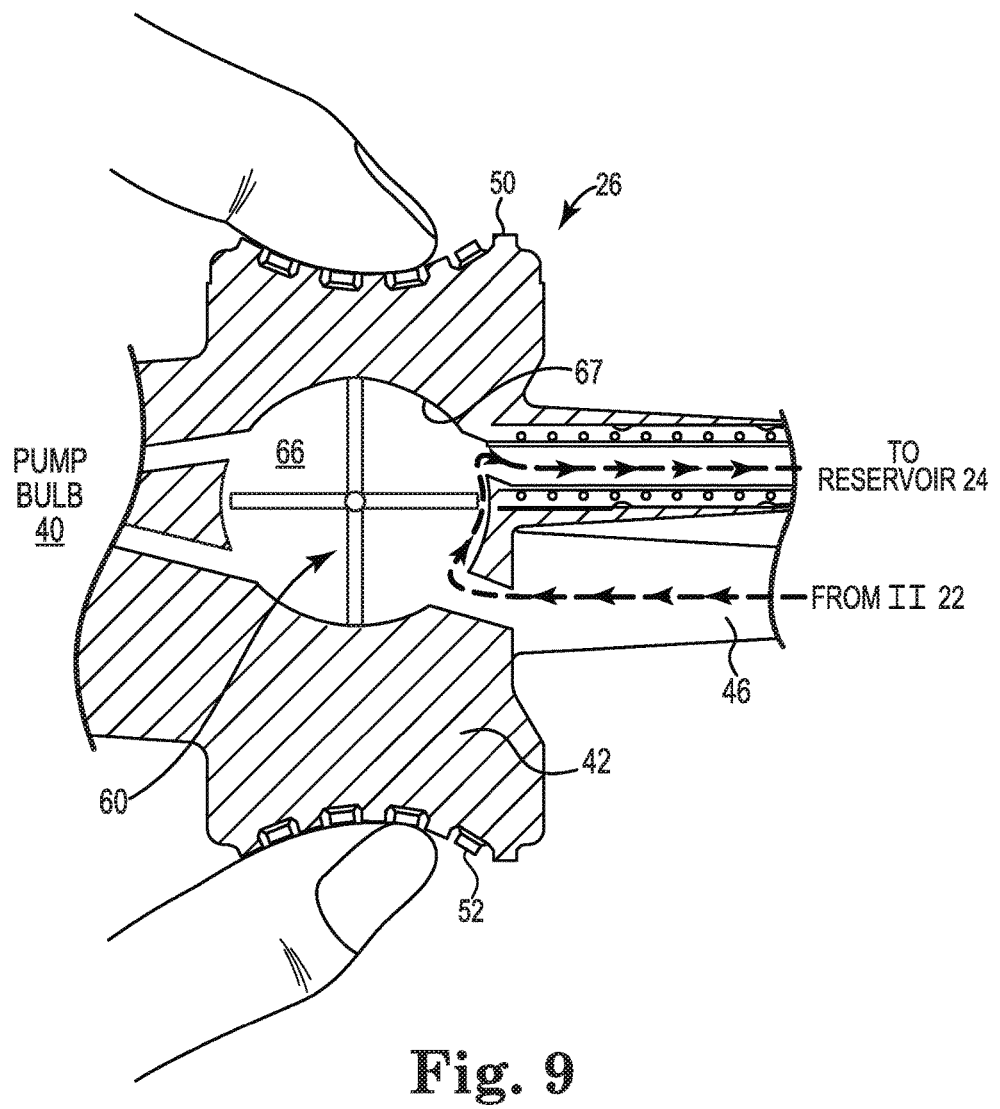
FIG. 9 is a partial cross-sectional side view of the pump illustrated in FIG. 4 showing one embodiment of a longitudinal deformation of a body of the pump.

FIG. 9 is a partial cross-sectional side view of a longitudinal deformation of the pump body 42. The user grips the deflation surfaces 50, 52 through the skin of the scrotum, while the surgeon contacts the deflation surfaces 50, 52 prior to complete implantation of the prosthetic. In any regard, the longitudinal force is applied to the deflation surfaces 50, 52, for example by a forefinger and a thumb. In one embodiment, the pump body 42 is fabricated from a material having a durometer (or a softness) that allows the body 42 to be deformable.

A liquid-tight seal is maintained between the rotary valve 60 and an internal wall inside of the body 42 of the pump, which prevents undesirable leaking and aids in pump efficiency. The body of the pump is deformable to break the liquid-tight seal between the rotary valve and the internal wall inside of the body of the pump. Deformation of the pump body 42 deforms the wall 67 of the recess 66, which breaks the seal between the valve 60 and the valve seat 67. The broken seal of the valve seat 67 allows the pressurized liquid in the inflatable implants 22 to flow between the valve 60 and the wall 67 and return to the reservoir 24. A silicone material having a durometer between 20-50 Shore A, preferably 25-40 Shore A, provides one suitable example of a material for the pump body 42. Other materials that allow the pump body 42 to be deformed manually by a force from the user's hand are also acceptable.

Adapting the pump body to be deformable to break the liquid-tight seal between the rotary valve and the internal wall inside of the body of the pump advantageously provides the user with a direct way to initiate deflation of the implants conveniently through the scrotum in accessing the implanted pump.

Figure 10A:
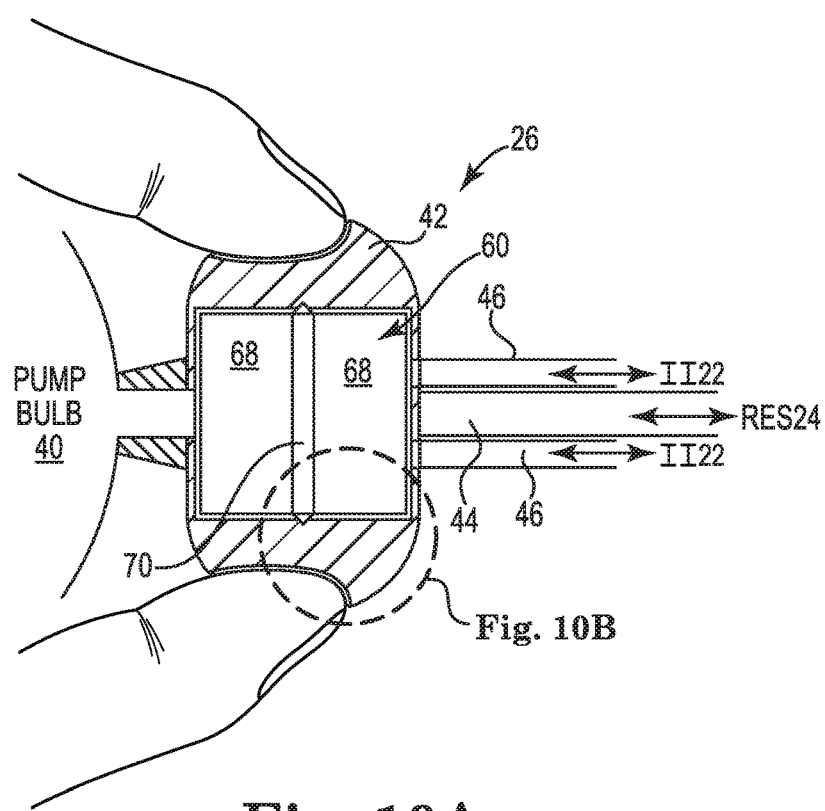
FIG. 10A is a partial cross-sectional top view of the pump illustrated in FIG. 4 showing one embodiment of a lateral deformation of a body of the pump.
Figure 10B:
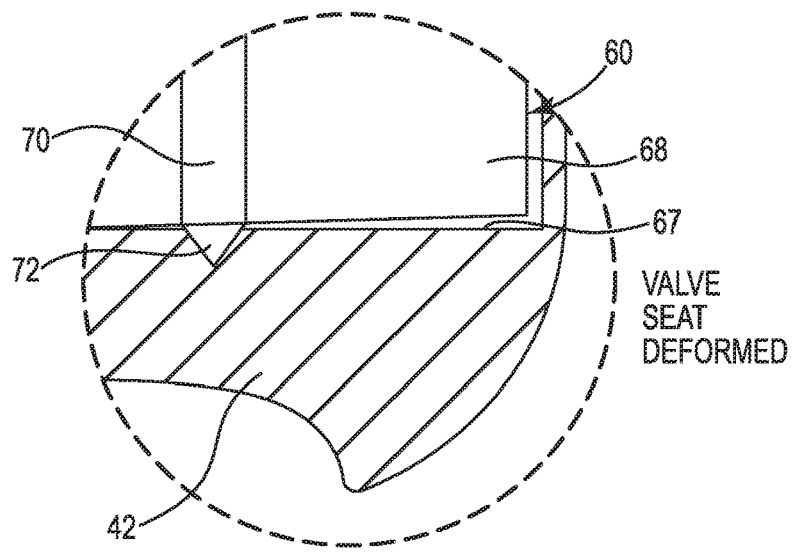
FIG. 10B is an enlarged view of a portion of the illustration of FIG. 10A.

FIG. 10A is a partial cross-sectional top view of a lateral deformation to the body 42 of the pump 26 causing the valve seat 67 to be deformed, and FIG. 10B is an enlarged view of the deformed valve seat 67. The user or the surgeon has imparted a lateral deformation to the body 42 of the pump 26 to deflate the implants 22. The deformation of the body 42 causes the wall 67 to deform, which creates a gap where the valve seat of the wall 67 has been separated away from the vane 68 of the valve 60. The pressurized liquid in the inflatable implants 22 naturally flows along the path of least resistance around the valve 60 and back to the reservoir 24.

Both of the longitudinal deformation of the pump body 42 and the lateral deformation of the pump body 42 gives rise to the deformation of the cylindrical recess, which advantageously allows the liquid to bypass the rotary valve 60 during the deflation of the inflatable implants 22.

FIG. 10C is a partial cross-sectional top view of one embodiment of the pump 26 illustrated in FIG. 4 showing an embodiment of an axel 73 providing lateral displacement of the valve 68 relative to the body 42 of the pump.

The user or the surgeon has squeezed the body 42 of the pump 26 to deflate the implants 22. The squeezing force imparts a "click" displacement to the valve 68 that is associated with a structure formed in an end portion of the axel 73. The axel 73 displaces the valve 68 laterally into a space 74, which creates a flow gap that allows the liquid to pass by the valve 68 and deflate the implants. The pressurized liquid in the inflatable implants 22 naturally flows along the path of least resistance around the valve 60 and back to the reservoir 24. A spring 75 allows for the displacement of the axel 73, which in turn pushes or displaces the valve 68 laterally into the space 74. The spring 75 can include a coiled spring disposed coaxially around the axel 73. Alternatively, the spring 75 can include forming a portion of the body 42 to be resilient and compressible to allow for the lateral displacement of the axel 73.

Thus, in the embodiment of FIG. 10C, the axel 73 provides a deflation valve or deflation assembly that is located in the body 42 of the pump 26 and integrated with the rotary valve 68. In one embodiment, the axel 73 provides a deflation valve or deflation assembly that is located in the body 42 of the pump 26 co-axial with a central rotating axis of the rotary valve 68. The embodiment of FIGS. 10C-E is useful when employed with the stop ledge 80 (FIG. 7) that prevents rotation of the rotary valve 68 in direction.

Locating the deflation assembly with the axis of the axel and the rotary valve advantageously packs several useful features into a smaller package that is more conveniently and efficiently implanted in the space within the scrotum of the patient.

FIG. 10D is a top view of the axel 73. The axel 73 includes alternating depressions, including a first depression 76 and a shorter second depression 77, and a pusher 78 that moves in an alternating fashion between the depressions 76, 77. The longer first depression 76 provides the axel 73 and the pump 26 with a steady-state. When the pusher 78 is seated in the first depression 76, the axel 73 is in a neutral position and the valve is sealed within the pump body 42. When the pusher is seated or engaged with the second depression 77, the axel is pushed and displaced laterally into the space 74 formed in the pump body 42 to provide the valve 68 with a deflation position. The "click" displacement is in reference to repeated squeezing of the ends of the pump body 42, where each squeeze clicks the valve 68 between its sealed neutral position and the displaced deflation position.

FIG. 10E is an enlarged view of the displaced valve 68. The pump body 42 has been squeezed to engage the pusher 78 with the shorter second depression 77, which acts to displace the valve 68 laterally into the space 74 (FIG. 10C). The effect of the first squeeze of the pump body 42 is to displace the valve 68 into the space 74 to occupy the deflation position, allowing the pressurized liquid in the implants to flow out of the implants, through the gap between the valve 68 and the pump body 42, and directly back to the reservoir, thus deflating the implants. A subsequent second squeeze seats the pusher 78 into the longer first depression 76, which allows the axel 73 to return to its neutral steady-state where the valve 68 is seated within the pump body 42. Alternating squeezing of the body 42 clicks the valve 68 between the deflation position where the valve 68 is displaced into the space 74 and the inflation position where the valve 68 is seated in its neutral position within the body 42.

Figure 11:
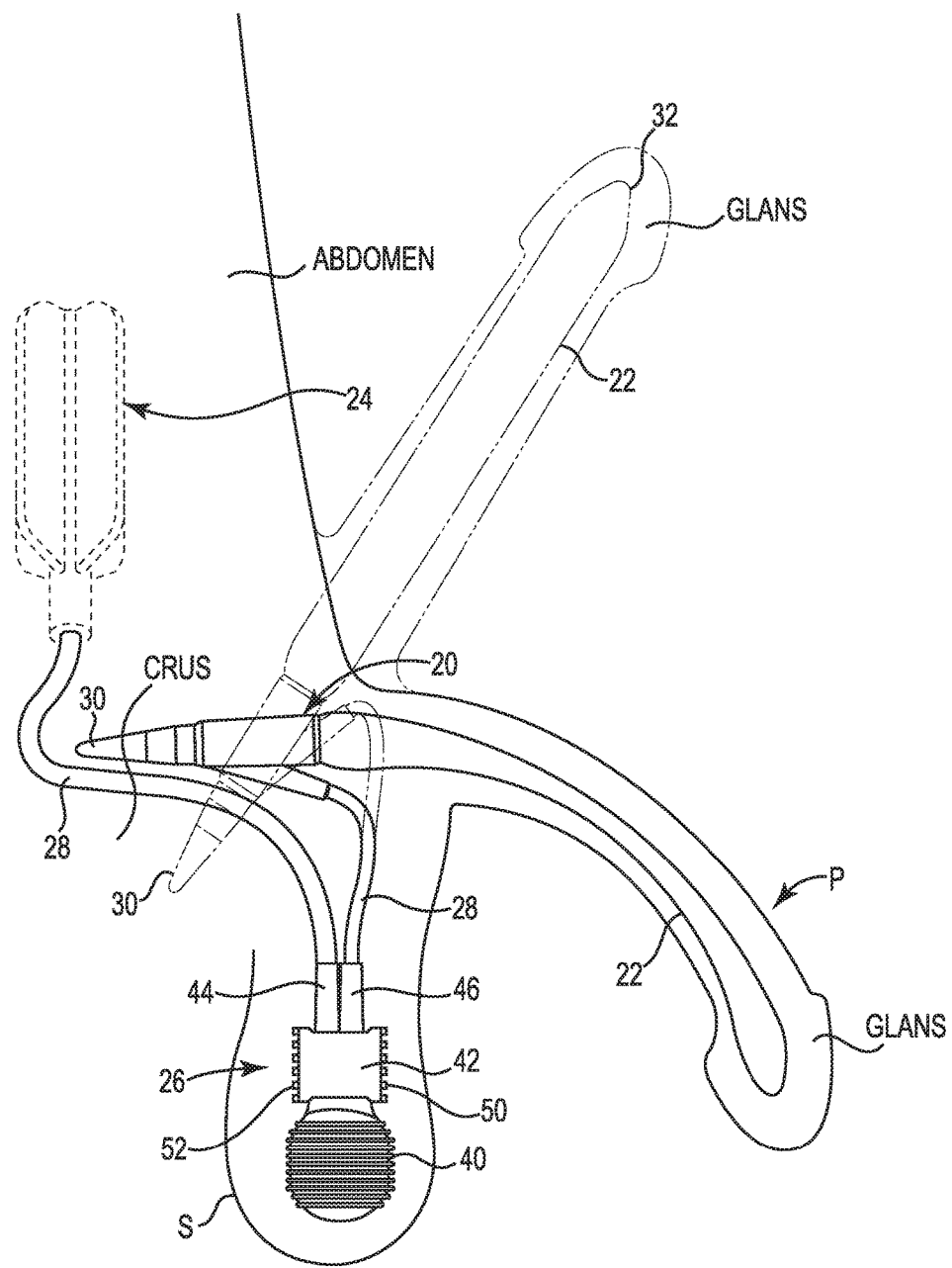
FIG. 11 is a schematic view of one embodiment of the penile prosthetic illustrated in FIG. 2 implanted into a user.

FIG. 11 is a schematic side view of the penile prosthetic 20 implanted in a user. The surgeon, or the surgical staff, opens a kit of parts containing the inflatable implants 22, the reservoir 24, the pump 26, tubing 28, and connectors for attaching the implants 22 and the reservoir 24 to the pump 26 with the tubing 28, and instructions for use (IFU). The IFU instructs the surgeon on where to locate incisions and where to place each component of the prosthetic 20 within the user.

The inflatable implants 22 are implanted in the penis P with the proximal end 30 inserted into the crus and the distal end 32 implanted within the glans. The reservoir 24 is implanted within the abdomen and the pump 26 is implanted within the scrotum S. The penile prosthetic 20 is operable consistent with the description above to inflate the inflatable implants 22 such that the penis P achieves an erect state. The deflation of the inflatable implants 22 operates as described in FIGS. 9-10B above to drain liquid out of the inflatable implants 22 and return the penis P to a flaccid state.

The IFU instruct the surgeon to 1) check for function of the rotary valve 60 to ensure that the valve is rotating to exhaust liquid into the implants, and 2) operating to prevent auto-inflation of the liquid from the reservoir directly to the implants with no squeezing of the pump bulb.

Figure 12:
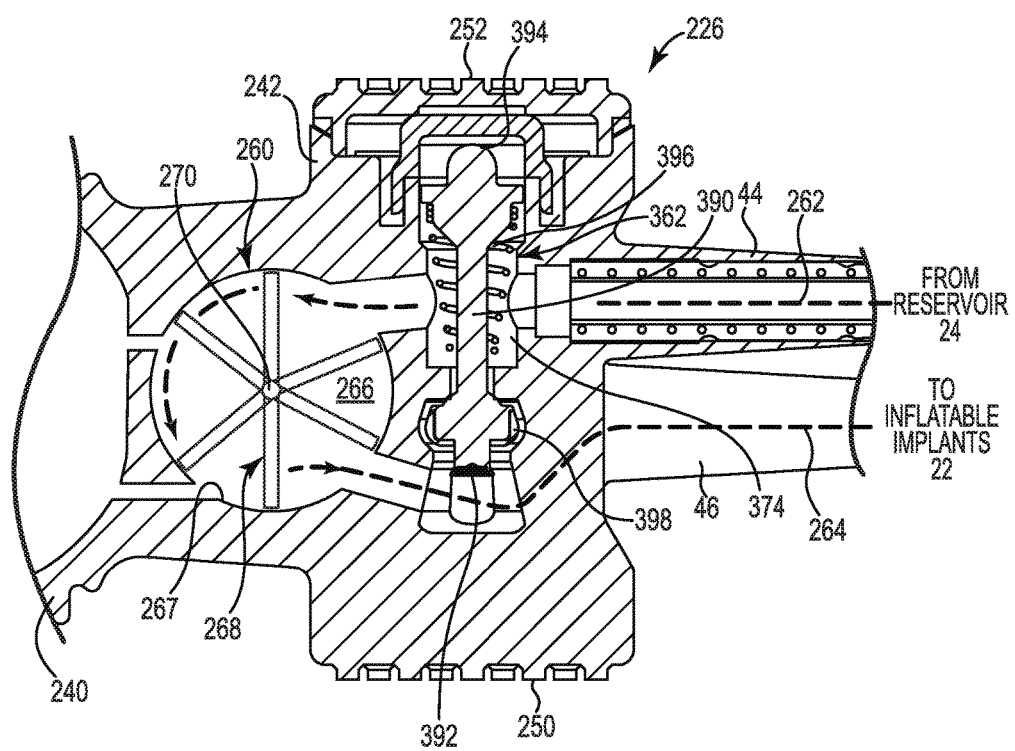
FIG. 12 is a partial cross-sectional view of one embodiment of a pump including a rotary inflation valve and a separate deflation valve, with the pump in an inflation mode.

FIG. 12 is a partial cross-sectional view of one embodiment of a pump 226 including a rotary inflation valve 260 and a separate deflation valve 362. The pump 226 is in an inflation mode after the pump bulb 240 has fully recovered.

The recovery of the pump bulb 240 creates suction inside the pump bulb 240. The suction forces the valve 260 to rotate in a counter clockwise direction directing liquid from the reservoir 24, along the flow path 262 and through the valve 260, through the pump bulb 240 and along the flow path 264, and into the inflatable implants 22. Subsequent squeezing or compression of the pump bulb 240 ejects the liquid in the pump bulb 240 through the flow path 264 and into the inflatable implants 22 for inflation of the implants. The valve 260 includes six vanes and is a uni-directional valve having s stop ledge, similar to the four-vane valve 26 described above in FIGS. 6 and 7.

A separate deflation valve 362 is located between deflation pads 250, 252 of the pump 226 and between the valve 260 and the tubing ports 44, 46. The deflation valve 362 is thus located in the body 242 of the pump 226 between the rotary valve 260 on one side and the reservoir tubing port 44 and the inflatable implant tubing port 46 on a second side. The deflation valve 362 includes a valve stem 390 extending between a first end 392 associated with the deflation pad 250, a second end 394 associated with the deflation pad 252, a spring 396 provided to bias the stem 390 relative to the pump body 242, and a crown 398 movably secured to the stem 390. In one embodiment, the spring 396 is a conical spring with one end of the spring wider than the other. Pushing on the deflation pads 250, 252 displaces the second end 394 of the stem away from the deflation pad 252.

The embodiment of FIG. 12 is useful when employed with the stop ledge 80 (FIG. 7) that prevents rotation of the rotary valve 268 in direction.

Figure 13:
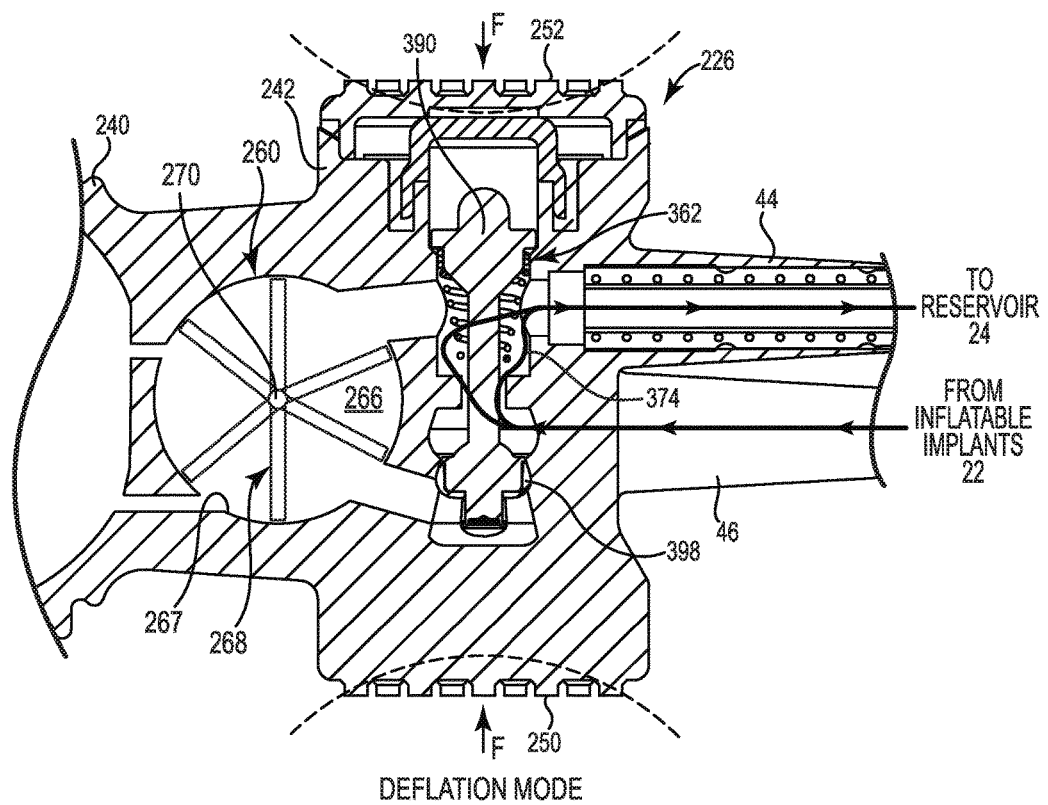
FIG. 13 is a partial cross-sectional view of the pump illustrated in FIG. 12, with the pump in a deflation mode.

FIG. 13 is a partial cross-sectional view of the pump 226 in a deflation mode. The body of the stem 390 and the spring 396 are located in a deflation flow path 374. During the deflation process, movement of the stem 390 displaces the crown 398 into a lower portion of the deflation flow path 374, which blocks a portion of the flow path 264, and opens the deflation flow path 374 for the flow of liquid from the inflatable implants 22 back to the reservoir 24.

The user is instructed to touch the deflation pads 250, 252 and apply a force F to compress the pads 250, 252. The compress force F displaces the stem 390 of the deflation valve 362 downward. Movement of the stem 390 downward results in the crown 398 being displaced downward to close the flow path 264 to the inflatable implants 22 and to open the deflation flow path 374 between the inflatable implants 22 and the reservoir 24.

The pressure of the liquid in the inflatable implants 22 is greater than the pressure in the empty reservoir 24. Thus, the liquid in the inflatable implants 22 flows out of the inflatable implants 22, through the deflation flow path 374, and enters the reservoir 24. The crown 398 has closed the flow path 264, but any liquid that might squeeze beyond the crown 398 would push the valve 260 in the clockwise direction, and the valve 260 is prevented from moving in the clockwise direction by the stop ledge described above in FIG. 7. Consequently, the liquid is constrained to flow only from the inflatable implants 22 to the reservoir 24 during deflation.

Although specific embodiments have been illustrated and described in this disclosure, it will be appreciated by those of ordinary skill in the art that a variety of alternate and/or equivalent implementations may be substituted for the specific embodiments shown and described without departing from the scope of this disclosure. This application is intended to cover any adaptations or variations of the above-disclosed medical devices. Therefore, it is intended that this invention is limited only by the claims and their equivalents.

What is claimed is:

1. A penile prosthesis kit of parts comprising:
an inflatable implant;
a reservoir adapted to contain a volume of liquid;
a pump;
tubing and tubing connectors provided for attachment of the inflatable implant and the reservoir to the pump; and
instructions for use provided for implantation and use of the pump;
wherein the pump has a rotary valve located in a first flow path entering into the pump and in a second flow path exiting from the pump, and when implanted, the rotary valve is constrained to rotate in only one direction to move a portion of the volume of the liquid from the reservoir through the first flow path and through the second flow path into the inflatable implant.

2. The penile prosthesis kit of parts of claim 1, wherein the rotary valve is constrained to rotate in only one direction to prevent auto-inflation of the inflatable implant.

3. The penile prosthesis kit of parts of claim 1, wherein the rotary valve is both an inflation valve adapted for inflation of the inflatable implant and an anti-auto-inflation valve adapted to prevent auto-inflation of the inflatable implant during pressurization of the reservoir.

4. The penile prosthesis kit of parts of claim 1, wherein an internal surface of the pump includes a stop ledge that engages with the rotary valve to prevent rotation of the rotary valve in one of a clockwise direction and a counter clockwise direction.

5. The penile prosthesis kit of parts of claim 1, wherein the rotary valve is located in a cylindrical recess formed in a body of the pump, and a wall of the cylindrical recess includes a stop ledge that engages with the rotary valve to prevent rotation of the rotary valve in one of a clockwise direction and a counter clockwise direction.

6. The penile prosthesis kit of parts of claim 1, wherein the rotary valve includes a plurality of vanes extending radially from a central axis of the rotary valve.

7. The penile prosthesis kit of parts of claim 1, wherein the pump includes a reservoir tubing port, an inflatable implant tubing port, and a pump bulb, and the reservoir tubing port and the inflatable implant tubing port are formed on a first side of the pump and the pump bulb is connected to a second side of the pump located opposite from the first side.

8. The penile prosthesis kit of parts of claim 1, wherein a liquid-tight seal is maintained between the rotary valve and an internal wall inside of a body of the pump, and the body of the pump is deformable to break the liquid-tight seal between the rotary valve and the internal wall inside of the body of the pump.

9. A penile prosthesis kit of parts comprising:
an inflatable implant;
a reservoir adapted to contain a volume of liquid;
a pump;
tubing and tubing connectors provided for attachment of the inflatable implant and the reservoir to the pump; and
instructions for use provided for implantation and use of the pump;
wherein the pump has a rotary valve located in a first flow path entering into the pump and in a second flow path exiting from the pump, and when implanted, the rotary valve is constrained to rotate in only one direction to prevent auto-inflation of the inflatable implant.

10. A penile prosthesis kit of parts comprising:
an inflatable implant;
a reservoir adapted to contain a volume of liquid;
a pump;

tubing and tubing connectors provided for attachment of the inflatable implant and the reservoir to the pump; and instructions for use provided for implantation and use of the pump;

wherein the pump has a rotary valve that is constrained to rotate in only one of a clockwise direction and a counter clockwise direction.

\* \* \* \* \*